US005928631A

United States Patent [19]
Lucas et al.

[11] Patent Number: 5,928,631
[45] Date of Patent: *Jul. 27, 1999

[54] METHODS FOR CONTROLLING ENVIRONMENTAL ODORS ON THE BODY USING COMPOSITIONS COMPRISING UNCOMPLEXED CYCLODEXTRINS

[75] Inventors: Juliet Marie Lucas, Cincinnati; Toan Trinh, Maineville, both of Ohio; Michael Thomas Dodd, Edgewood, Ky.; Robert Gregory Bartolo, Cincinnati, Ohio

[73] Assignee: The Procter & Gamble Company, Cincinnati, Ohio

[*] Notice: This patent is subject to a terminal disclaimer.

[21] Appl. No.: 08/871,854

[22] Filed: Jun. 9, 1997

[51] Int. Cl.⁶ ..................................................... A61K 7/00
[52] U.S. Cl. .............................. 424/65; 424/67; 424/69; 424/78.03; 424/401; 424/405; 424/642; 424/715; 424/717; 422/5
[58] Field of Search .............................. 424/65, 67, 69, 424/78.03, 401, 405, 642, 715, 717; 422/5

[56] References Cited

U.S. PATENT DOCUMENTS

| | | | |
|---|---|---|---|
| 2,544,093 | 3/1951 | Kilgore | 252/1 |
| 3,074,891 | 1/1963 | Kulka | 252/305 |
| 4,278,658 | 7/1981 | Hooper et al. | 424/65 |
| 4,382,079 | 5/1983 | Marschner | 424/65 |
| 4,822,602 | 4/1989 | Sabatelli | 424/65 |
| 4,904,524 | 2/1990 | Yoh | 428/311.3 |
| 5,429,628 | 7/1995 | Trinh et al. | 604/359 |
| 5,486,355 | 1/1996 | Berschied, Jr. | 424/65 |
| 5,512,199 | 4/1996 | Khan et al. | 252/106 |
| 5,514,367 | 5/1996 | Lentini et al. | 424/59 |
| 5,518,727 | 5/1996 | Lajoie et al. | 424/400 |
| 5,552,378 | 9/1996 | Trinh et al. | 512/3 |
| 5,578,563 | 11/1996 | Trinh et al. | 510/513 |
| 5,580,851 | 12/1996 | Trinh et al. | 512/4 |
| 5,593,670 | 1/1997 | Trinh et al. | 424/76.1 |
| 5,635,165 | 6/1997 | Panitch | 424/65 |
| 5,663,134 | 9/1997 | Trinh et al. | 510/406 |
| 5,670,475 | 9/1997 | Trinh et al. | 510/470 |

FOREIGN PATENT DOCUMENTS

| | | |
|---|---|---|
| 0 613 675 A1 | 9/1994 | European Pat. Off. . |
| 2201880 | 5/1974 | France . |
| 2731520 | 1/1979 | Germany . |
| 208482 | 8/1992 | Hungary . |
| 53-41440 | 4/1978 | Japan . |
| 58-124452 | 7/1983 | Japan . |
| 61-128973 | 6/1986 | Japan . |
| 63-164953 | 7/1988 | Japan . |
| 3-170415 | 7/1991 | Japan . |
| 3-284616 | 12/1991 | Japan . |
| 5-269185 | 10/1993 | Japan . |
| WO 95/17175 | 6/1995 | WIPO . |

OTHER PUBLICATIONS

Hashimoto, H., "Studies on the Industrial Production and Application of Cyclodextrins", Starch Science, vol. 36, No. 1 (1989), pp. 35–42.

Hashimoto, H., "Application of Cyclodextrins to Foods, Toiletries and Other Products in Japan", Ensuiko Sugar Refining Co., Ltd., pp. 13–46.

U.S. application No. 08/736,469, Trinh et al., filed Oct. 24, 1996.
U.S. application No. 08/736,093, Trinh et al., filed Oct. 24, 1996.
U.S. application No. 08/889,607, Trinh et al., filed Jul. 8, 1997.
U.S. application No. 08/736,471, Lucas et al., filed Oct. 24, 1996.
U.S. application No. 08/736,470, Lucas et al., filed Oct. 24, 1996.
U.S. application No. 08/738,964, Dodd et al., filed Oct. 24, 1996.
U.S. application No. 08/736,838, Peterson et al., filed Oct. 28, 1996.
U.S. application No. 08/739,091, Peterson et al., filed Oct. 28, 1996.
U.S. application No. 08/871,166, Lucas et al., filed Jun. 9, 1997.
U.S. application No. 08/871,791, Dodd et al., filed Jun. 9, 1997.
U.S. application No. 08/871,855, Trinh et al., filed Jun. 9, 1997.
U.S. application No. 08/871,853, Lucas et al., filed Jun. 9, 1997.
U.S. application No. 08/871,857, Lucas et al., filed Jun. 9, 1997.
U.S. application No. 08/871,790, Peterson et al., filed Jun. 9,1997.
U.S. application No. 08/871,856, Peterson et al., filed Jun. 9, 1997
U.S. application No. 08/871,858, Lucas et al., filed Jun. 9, 1997.
U.S. application No. 08/871,577, Lucas et al., filed Jun. 9, 1997.
U.S. application No. 08/871,860, Lucas et al., filed Jun. 9, 1997.

(List continued on next page.)

Primary Examiner—Nathan M. Nutter
Attorney, Agent, or Firm—Kirsten K. Stone; Mary Catherine Hentz; Douglas C. Mohl

[57] ABSTRACT

The present invention encompasses a method of controlling environmental malodors on the body comprising the application to the skin of a composition comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, and skin protectants; one or more surfactants each having a hydrophilic/lipophilic balance of about 8 to 18 and wherein each surfactant, when combined with an aqueous cyclodextrin solution, provides no less than 25% of odor capture as an aqueous cyclodextrin solution; and an aqueous carrier. The compositions can be applied directly as a spray, poured from a bottle and applied by hand, or applied via a wipe.

16 Claims, No Drawings

OTHER PUBLICATIONS

U.S. application No. 08/871,861, Peterson et al., filed Jun. 9, 1997.
U.S. application No. 08/871,092, Peterson et al., filed Jun. 9, 1997.
U.S. application No. 08/289,732, Trinh et al., filed Aug. 12, 1994.
U.S. application No. 08/289,733, Trinh et al., filed Aug. 12, 1994.
U.S. application No. 08/289,734, Cappel et al., filed Aug. 12, 1994.
U.S. application No. 08/289,735, Cappel et al., filed Aug. 12, 1994.
U.S. application No. 08/289,969, Pilosof et al., filed Aug. 12, 1997.
U.S. application No. 08/871,576, Woo et al., filed Jun. 9, 1997.
U.S. application No. 08/871,119, Woo et al., filed Jun. 9, 1997.
U.S. application No. 08/871,042, Woo et al., filed Jun. 9, 1997.

METHODS FOR CONTROLLING ENVIRONMENTAL ODORS ON THE BODY USING COMPOSITIONS COMPRISING UNCOMPLEXED CYCLODEXTRINS

BACKGROUND OF THE INVENTION

Daily contact with substances which leave unpleasant and/or lingering odors on an individual's body and hair is almost unavoidable. Foods such as fish, onions, garlic or other spices, cooking odors, smoke, tobacco, and gasoline are just a few of the common environmental sources of malodors in daily life.

Numerous attempts have been made to conceal unpleasant odors through the use of deodorizing compositions. These compositions typically rely on the presence of heavy fragrances or perfumes to mask odors. Not only are such perfumes and fragrances often inadequate at fully concealing malodors, very often they are irritating to the user.

Zeolites such as those marketed under the trade name Abscents® by the Union Carbide Corporation and UOP are known odor absorbers. However these commonly known solid odor absorbers, in addition to known activated charcoal odor absorbers, lose functionality when wet. Therefore, when wetted by body fluids or when carried in an aqueous solution, these odor absorbers are not preferred as they lose their desired odor absorbent characteristics. Furthermore, zeolites can cause a "harsh" feel if too much is deposited onto the skin. The white zeolite powder and the black activated charcoal can also be rather visible and unsightly when applied on surfaces such as the skin.

U.S. Pat. No. 5,534,165, to Pilosof et al., issued Jul. 9, 1996, describes aqueous, odor absorbing compositions for controlling odors on fabrics, particularly clothes. Such compositions, however, are not for use directly on the human skin.

Thus, there remains a need for improved methods for controlling odors which are safe and effective for use on the entire body. More particularly, there is a need for convenient methods of absorbing a broad spectrum of odors that are not fully suppressed by the aforementioned means.

It has been discovered that methods for such enhanced malodor control can be safely provided to the entire body by application of a leave-on mixture which incorporates odor absorbing, uncomplexed cyclodextrins into an aqueous solution. Furthermore, a method of controlling malodor has been discovered comprising the application of uncomplexed cyclodextrins and other optional components. Such methods provide a leave-on skin solution with optimal malodor absorbing characteristics. Moreover, it has been discovered that the aforementioned benefits may be delivered in a mixture which also optionally delivers skin aid benefits to the user such as protection and/or moisturization.

These and other objects of the present invention will become readily apparent from the detailed description which follows.

All percentages, ratios, and parts herein, in the Specification, Examples, and Claims are by weight unless otherwise stated. The term "g", as used herein, means gram. The term "ml", as used herein, means milliliter. The term "wt", as used herein means weight.

SUMMARY OF THE INVENTION

The present invention encompasses a method of controlling malodors on skin comprising the application to the skin of a composition comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, and skin protectants; one or more surfactants each having a hydrophilic/lipophilic balance of about 8 to 18 and wherein each surfactant, when combined with an aqueous cyclodextrin solution, provides no less than 25% of odor capture as an aqueous cyclodextrin solution; and an aqueous carrier.

DETAILED DESCRIPTION OF THE INVENTION

The methods for controlling environmental malodors comprising the application of a if perfume-free, malodor-absorbing composition. The compositions can be applied directly as a spray, poured from a bottle and applied by hand, or applied via a pre-formed wipe which is wet with the composition when it is applied to skin or hair. The present invention also relates to an article of manufacture comprising the environmental odor-absorbing composition incorporated into a flexible dispensing means.

The term "environmental malodors", as used herein means any odor which may be on a human or mammal which is not the result of human or mammalian body odor and/or body fluids. Such odors include but are not limited to odors from foods such as fish, garlic, onions, peppers and spices; cooking; smoke; tobacco; gasoline; and the like.

The term "body fluids", as used herein, includes eccrine sweat, apocrine sweat, sebum, build up of sensible moisture from transepidermal water loss, vaginal discharge, urine, and mixtures thereof. The term "body odor", as used herein, means odors which are generated as a result of the natural functioning of a human or mammalian body. Such odors include, but are not limited to odors produced by microorganisms of the human mammalian skin (i.e. bacterial decomposition of skin secretions), urine, or vaginal discharge, and mixtures thereof. The term "entire body" means the entire external surface of human or mammalian skin. The term "skin" means human or mammalian skin.

A detailed description of essential and optional components of the present invention is given below.

METHODS OF USE

The present invention encompasses a method of controlling environmental malodors on skin comprising the application to skin of a composition comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, and skin protectants; one or more surfactants each having a hydrophilic/lipophilic balance of about 8 to 18 and wherein each surfactant, when combined with an aqueous cyclodextrin solution, provides no less than 25% of odor capture as an aqueous cyclodextrin solution; and an aqueous carrier. These compositions may also optionally comprise one or more of the following: hydrophobic antimicrobials; water-soluble antimicrobial preservatives; low molecular weight polyols; zinc salts; water-soluble polymers; soluble carbonate and/or bicarbonate salts; chelating agents; zeolites; activated carbon; and mixtures thereof.

An "effective amount" of the compositions of the present invention, as used herein, means an amount sufficient to absorb odor to the point that it is less noticeable by the human sense of smell. While the determination of an effective amount used and the number of uses per day is ultimately left to the discretion of the user, typically an effective amount will be from about 0.05 grams to about 3.0 grams of environmental odor-absorbing composition per use, applied from about 1 to about 15 times per day, for as many days as desired by the user.

The compositions of the present invention are topically applied directly to the skin or hair. The compositions can be delivered by placing the composition into a dispensing means and applying an effective amount via spraying or rubbing the composition onto the desired skin surface; typically the entire body. Preferably the dispensing means is a wipe or a spray dispenser. Distribution of the composition of the present invention can also be achieved by using a pre-formed applicator such as a roller, pad, sponge, tissue, cotton ball, hand, etc.

Alternatively, the user may combine the composition of the present invention with a wipe substance of his or her own choosing. To do this, the user simply chooses a wipe substance such as a commercial paper towel, tissue, sponge, cotton, pad, washcloth, or the like; and pours, from a bottle or other suitable container, a solution of the composition of the present invention over the chosen wipe substance and applies the composition to the desired area of the body. In this manner, the user may use as much or as little of the composition of the present invention as he/she desires, depending upon their intended use and degree of odor control necessary.

Cyclodextrin

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of 1% (1 gram in 100 grams of water).

Non-derivatised beta-cyclodextrin can be present at a level up to its solubility limit of about 1.85% at room temperature. When beta-cyclodextrin is applied to a wipe substrate, levels higher than its solubility limit can be used.

Preferred, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Highly water-soluble cyclodextrins are those having water solubility of at least about 10 g in 100 ml of water at room temperature, preferably at least about 20 g in 100 ml of water, more preferably at least about 25 g in 100 ml of water at room temperature. The preferred highly water-soluble cylcodextrins are hydroxy propyl beta-cyclodextrin and methylated beta-cyclodextrin.

It is also preferable to use a mixture of cyclodextrins. Such mixtures absorb environmental odors on the body more broadly by complexing with a wider range of odoriferous molecules having a wider range of molecular sizes. Preferred are mixtures of beta-cyclodextrin and/or its derivatives with alpha-cyclodextrin and/or its derivatives, and mixtures thereof. The levels of cyclodextrin are from about 0.1% to about 5%, preferably from about 0.2% to about 4%, more preferably from about 0.3% to about 3%, most preferably from about 0.4% to about 2%, by weight of the composition.

Concentrated compositions can also be used. When a concentrated product is used, i.e., when the level of cyclodextrin used is from about 3% to about 10%, it is preferable to dilute the composition before applying to the skin in order to avoid tacky skin feel and/or an undesirable amount of residue. Preferably the cyclodextrin is diluted with about 50% to about 2000%, more preferably with about 60% to about 1000%, most preferably with about 75% to about 500%, by weight of the composition of water.

The complexation between cyclodextrin and odorous molecules occurs rapidly in the presence of water when the solubilized cyclodextrins are first applied to the skin. Additionally, cyclodextrins which dry on the skin surfaces will once again achieve enhanced absorption capabilities when rewetted with fluids. This is convenient for the user because the cyclodextrins, while on dry skin, will not readily fill their cavities with other odors which would otherwise render them less efficient. More particularly, upon solubilization of the cyclodextrins by body fluids or other fluids, the isolated cavities again become available to form inclusion complexes with the environmental odor molecules on the body. Thus, ultimately, the availability of solubilized uncomplexed cyclodextrin is essential for an effective and efficient odor control performance. A more complete description of the cyclodextrins and cyclodextrin derivatives useful in the present invention can be found in U.S. Pat. No. 5,534,165, Pilosof et al., issued Jul. 9, 1996, which is incorporated herein by reference in its entirety.

Oil Phase

The present invention method also includes compositions comprising an oil phase. The oil phase is chosen from the following ingredients: skin protectants, emollients, and/or moisturizers. Saturated or hydrogenated oils are preferred. These ingredients enhance the skin feel characteristics and/or skin care benefits of the present invention. Additionally, the oil phase provides a medium in which hydrophobic antibacterials, if present, may be dissolved.

Skin protectant ingredients can prevent or reduce chafing, skin irritation and/or skin friction that may occur between skin-to-skin contact sites. Preferred skin protectants useful in the present invention include, but are not limited to: vitamin A, cod liver oil, cocoa butter, shark liver oil, dimethicone, petrolatum, white petrolatum, mineral oil, jojoba oil, and lanolin. More preferred are dimethicone, petrolatum, white petrolatum, mineral oil, jojoba oil, and lanolin. Most preferred is dimethicone.

Moisturizers can aid in adding moisture to the skin may be included in the oil carrier of the present invention. Preferred moisturizers useful in the present invention include, but are not limited to vegetable oils and mineral oil. More preferred are hydrogenated or saturated vegetable or mineral oils. Other moisturizers useful in the present invention can be chosen from the oily moisturizers in

TABLE 1

| | | |
|---|---|---|
| Acetamido propyl trimonium chloride | Hybrid safflower oil | PEG-6 |
| Adenosine triphosphate | Hydrogenated lecithin | PEG-8 |
| Algae extract | Hydrolyzed polyisobutene | PEG-12 |
| Algae extract (*Fucus vesiculosus*) | Hydrolyzed elastin | PEG-100 stearate |
| Aloe | Hydrolyzed fibronectin | Perfluoropolymethyl-isopropyl ether |
| Aloe vera | Hydrolyzed glycosaminoglycans | Petrolatum |
| Aloe vera gel condensed | Hydrolyzed keratin | Petroleum wax |
| Aloe vera gel, decolorized | Hydrolyzed placental protein | Pistachio nut oil |
| Aloe vera gel, food grade | Hydrolyzed serum protein | Placental protein, water soluble |
| Aloe vera gel freeze-dried powder | Hydrolyzed silk | Plankton extract |
| Amnoitic fluid | Hydrolyzed wheat protein | Polyamino sugar condensate |
| Arginine PCA | Inositol | Polybutene |
| Atelocollagen | Isostearyl hydrolyzed animal protein | Polyglyceryl methacrylate |
| Avocado oil | Jojoba esters | Potassium DNA |
| Brazil nut oil | Jojoba oil | Potassium PCA |
| C10-30 cholesterol-lanosterol esters | Keratin amino acids | PPG-8-SMDI copolymer |
| Calcium protein complex | Kiwi extract | PPG-10 butanediol |
| Carrigeenan extract (*Chondrus crispus*) | Konjac mannan | PPG-12SMDI copolymer |
| Chia oil (*Salvia hispanica*) | Lactamide MEA | PPG-20 methyl glucose ether distearate |
| Chitin | Lactcoccus hydrolysate | PPG-51-SMDI copolymer |
| Chitosan | Lactoylmethylsilanol elastinate | Rehmannia root extract |
| Chitosan PCA | Lanolin alcohol | Rice bran oil |
| Cholesteric esters | Lauryl PCA | Rose seed extract |
| Cholesterol | Lecithin | Royal jelly extract |
| Chondroitin sulfate | Lesquerella oil | Saccharide isomerate |
| Collagen acids | Liposomes | Selenium aspartate |
| Collagen amino acids | Live yeast cells derivative liposome | Selenium protein complex |
| Copper aspartate | Lysine PCA | Serum albumin |
| Copper protein complex | Magnesium aspartate | Silk amino acids |
| Desamido collagen | Maltitol | Sodium chondroitin sulfate |
| Dibenzylidene sorbitol | Manganese aspartate | Sodium DNA |
| Dimethyl hyraluronate | Marine polyaminosaccharide | Spherical cellulose acetate |
| Dimethylsilanol hyaluronate | Methylsilanol elastinate | Squalene |
| Dioctyl maleate | Methylsilanol mannuronate | Stomach extract |
| Dipentaerythritol fatty acid ester | Mineral oil | Super oxide dismutase |
| Elastin amino acids | Molybdenum aspartate | Super oxide dismutase liposome[1] |
| Ethyl minkate | Neopentyl glycol dicaprate | Tissue extract |
| Ethyl panthenol | Oat β-glucan | Tocopheryl acetate |
| Evening primrose | *Ophiopogon japonicus* extract | Tocopheryl linoleate |
| Glycereth-12 | Orange wax | Tomato extract (*Solanum lycopersicum L.*) |
| Glycosaminoglycans | Palmetto extract | Trimethylglycine |
| Glycosphingolipids | Pantethine | Yogurt filtrate |
| Honey extract | Paraffin | Zinc aspartate |
| Hyaluronic acid | PEG-4 | |

Emollients for softening and soothing of skin are also useful in the present invention. Emollients useful herein include tocopherol or tocopherol acetate, triglycerides, vegetable oils, or mineral oil. Other emollients useful in the present invention can be chosen from the oily emollients in

TABLE 2

| | | |
|---|---|---|
| Acetylated glycol stearate | C14-15 alcohols | Coconut oil |
| Acetylated hydrogenated lanolin | Camellia oil, (*Camellia japonica*) | Coco rapeseedate |
| Acetylated hydrogenated lard glyceride | Canola oil | Colloidal oatmeal |
| Acetylated hydrogenated vegetable glyceride | Caprylic-capric-linoleic triglyceride | Corn oil |
| Acetylated lanolin | Caprylic-capric-stearic triglyceride | Cottonseed oil |
| Acetylated lanolin alcohol | Caprylic-capric-succinic triglyceride | Cuttlefish extract |
| Acetylated lard glyceride | Caprylic-capric triglyceride | Cyclomethicone |
| Acetylated palm kernel glycerides | Caprylic-capric triglyceride PEG-4 esters | Decamethyl cyclopentasiloxane |
| Aluminum magnesium hydroxy stearate | *Capisicum oleoresin* (*Capsicum frutescens L.*) | Deceth-4 phosphate |
| AMP-isostearoyl hydrolyzed soy protein | Cashew oil | Decyl oleate |
| Apricot kernel oil | Castor oil | Decyl tetradecanol |
| Arachidyl behenate | Cetearyl behenate | Decyl tetradecanol |
| Argana oil | Cetearyl candelillate | Dialkyldimethylpolysiloxane |
| Avocado oil | Cetearyl isononanoate | Dibutyl sebacate |

TABLE 2-continued

| | | |
|---|---|---|
| Avocado oil ethyl ester | Cetearyl octanoate | Dicapryl adipate |
| Avocado oil unsaponifiables | Cetearyl palmitate | Diethylene glycol diisononanoate |
| Babassu oil | Cetearyl stearate | Diethylene glycol dioctanoate |
| Batyl isostearate | Ceteth-10 | bis-Diglyceryl-caprylate-caprate-isostearate-hydroxystearate-adipate |
| Batyl stearate | Cetostearyl stearate | bis-Diglyceryl-caprylate-caprate-isostearate-stearate-hydroxystearate-adipate |
| Behenamidopropyl dihydroxypropyl dimonium chloride | Cetyl acetate | Dihydroabietyl behenate |
| Behenoxy dmethicone | Cetyl alcohol | Dihydroxyethyl tallow amine oleate |
| Behenyl alcohol | Cetyl C12-15 nareth-9 carboxylate | Diisobutyl adipate |
| Behenyl behenate | Cetyl caprylate | Diisocetyl adipate |
| Behenyl erucate | Cetyl esters | Diisopropyl adipate |
| Behenyl isostearate | Cetyl lactate | Diisopropyl dilinoleate |
| Benzyl laurate | Cetyl myristate | Diisopropyl dimer dilinoleate |
| Borage seed oil (*Borago officinalis*) | Cetyl octanoate | Diisopropyl sebacate |
| Brain extract | Cetyl oleate | Diisostearyl adipate |
| Brazil nut oil | Cetyl palmitate | Diisostearyl dimer dilinoleate |
| Butyl myristate | Cetyl PPG-2 isodeceth-7 carboxylate | Diisostearyl fumerate |
| 2-Butyl octanol | Cetyl ricinoleate | Diisostearyl malate |
| Butyloctyl oleate | Cetyl stearate | Dilinoleic acid |
| Butyl oleate | Cetyl stearyl octanoate | Dimethicone |
| Butyl stearate | Cherry pit oil | Dimethicone propylethylenediamine behenate |
| C10-18 triglycerides | Chia oil (*Salvia hispanica*) | Dioctyl adipate |
| C10-30 cholesterol-lamosterol esters | Cholesteric esters | Dioctylcyclohexane |
| C12-13 alcohols | Cholesterol | Dioctyl dimer dilinoleate |
| C12-15 alcohols | Cholesteryl hydroxy stearate | Dioctyl malate |
| C12-15 alkyl benzoate | Cholesteryl stearate | Dioctyl maleate |
| dl-C12-15 Alkyl fumarate | Choleth-24 | Dioctyl sebacate |
| C12-15 alkyl lactate | Cocamidopropyl PG-dimonium chloride | Dioctyl succinate |
| C12-15 linear alcohols 2-ethylhexanoate | Cocoa butter | Dipentaerythritol fatty acid ester |
| C12-16 alcohols | Coco-caprylate-caprate | Dipentairythrityl hexacaprate-hexacaprylate |
| C12-18 triglycerides | Coco-hydrolyzed soy protein | Dipentaethylthrite hexahydroxystearate-isostearate |
| Distearyldimethylamine dilinoleate | Hybrid safflower oil | Isoeicosane |
| Ditridecyl adipate | Hydrogenated C6-C14 olefin polymers | Isohexadecane |
| 1-Docosanol | Hydrogenated castor oil | Isononyl isononanoate |
| Egg yolk extract | Hydrogenated castor oil laurate | Isooctadecyl hexadecanoate |
| Erucyl erucate | Hydrogenated coconut oil | Isopentacontaoctane |
| Ethyl avocadate | Hydrogenated cottonseed oil | Isopentyldiol |
| 2-Ethythexyl hexadecanoate | Hydrogenated lanolin | Isopropyl avocadate |
| Ethylhexyl isopalmitate | Hydrogenated lanolin, distilled | Isopropyl C12-15 pareth-9-carboxylate |
| 2-Ethylhexyl isostearate | Hydrogenated milk fat | Isopropyl isostearate |
| Ethyl linoleate | Hydrogenated mink oil | Isopropyl lanolate |
| Ethyl minkate | Hydrogenated palm kernel glycerides | Isopropyl linoleate |
| Ethyl morbuate | Hydrogenated palm oil | Isopropyl myristate |
| Ethyl myristate | Hydrogenated polyisobutene | Isopropyl palmitate |
| Ethyl oleate | Hydrogenated soybean oil | Isopropyl PPG-2-isodeceth-7 carboxylate |
| Ethyl olivate | Hydrogenated Starch hydrolysate | Isopropyi stearate |
| Evening primrose oil (*Oenothera spp*) | Hydrogenated tallow glyceride | Isosorbide laurate |
| Glycereth-5 lactate | Hydrogenated tallow glyceride lactate | Isostearic acid |
| Glycereth-7 benzoate | Hydrogenated turtle oil | Isostearyl alcohol |
| Glycereth-7 diisononoate | Hydrogenated vegetable glycerides | Isostearylamidopropyl dihydroxypropyl dimonium chloride |
| Glycereth-7 triacetate | Hydrogenated vegetable oil | Isostearyl behenate |
| Glycereth-7 trioctanoate | Hydrolyzed conchiolin protein | Isostearyl benzoate |
| Glycereth-12 | Hydrolized keratin | Isostearyl diglyceryl succinate |
| Glycereth-26 | Hydrolized oat protein | Isostearyl erucate |
| Glycerol tricaprylate-caprate | Hydroxylated lanolin | Isostearyl erucyl erucate |
| Glyceryl adipate | Hydroxylated milk glycerides | Isostearyl isostearate |
| Glyceryl dioleate | Hydroxystearic acid | Isostearyl lactate |
| Glyceryl isostearate | Illipe butter | Isostearyl malate |
| Glyceryl lanolate | Isobutyl palmitate | Isostearyl myristate |
| Glyceryl linoleate | Isobutyl stearate | Isostearyl neopentanoate |
| Glyceryl monopyroglutamate | Isocetyl behenate | Isostearyl palmitate |
| Glyceryl myristate | Isocetyl octanoate | Isostearyl stearoyl stearate |
| Glyceryl oleate | Isocetyl palmitate | Isotridecyl cocoate |
| Glyceryl ricinoleate | Isocetyl salicylate | Isotridecyl isononanoate |
| Glyceryl triacetyl hydroxystearate | Isocetyl stearate | Isotridecyl myristate |

TABLE 2-continued

| | | |
|---|---|---|
| Glyceryl triacetyl ricinoleate | Isodecyl citrate | Jojoba butter |
| Glycosaminoglycans | Isodecyl cocoate | Jojoba esters |
| Glycosphingolipids | Isodecyl hydroxypropanetricarboxylic acid | Jojoba oil, synthetic |
| Grape seed oil | Isodecyl isononanoate | Kalaya oil |
| Hazelnut oil | Isodecyl laurate | Kukui nut oil |
| Hexadecyl isopalmitate | Isodecyl neopentanoate | Lactamide DGA |
| Hexamethyldisiloxine | Isodecyl octanote | Lactic acid monoethanolamide |
| Hexyidecanol | Isodecyl oleate | Laneth-10 acetate |
| Hexyl laurate | Isodecyl salicylate | Lanolin |
| Honey extract | Isodecyl stearate | Lanolin acid |
| Lanolin alcohol | Neopentylglycol dicaprate-dicaprylate | Peanut oil |
| Lanolin oil | Neopentylglycol diisooctanoate | PEG-2 Diisonanoate |
| Lanosterol | Neopentyl glycol dioctanoate | PEG-2 dioctanoate |
| Lard glyceride | Oat flour | PEG-2 milk solids |
| Laureth-2 | Oat protein | PEG-4 |
| Laureth-2 acetate | Octacosanyl stearate | PEG-4 diheptanoate |
| Laureth-2 benzoate | Octyl cocoate | PEG-4 dilaurate |
| Laureth-2 octanoate | Octyl decanol | PEG-5 C8-12 alcohols citrate |
| Laureth-3 | Octyl dodecanol | PEG-5 C14-18 alcohols citrate |
| Lauryldimethylamine isostearate | Octyl dodecyl behenate | PEG-5 hydrogenated castor oil |
| Lauryldimethylamine oleate | Octyidodecyl benzoate | PEG-5 hydrogenated castor oil triisostearate |
| Lauryl lactate | Octyidodecyl erucate | PEG-6 |
| Lauryl phosphate | 2-Octyidodecyl erucate | PEG-8 |
| Lesquerella oil | 2-Octyidodecyl lactate | PEG-8 dilaurate |
| Linoleic acid | Octyidodecyl myristate | PEG-8 dioleate |
| Macadamia nut oil | 2-Octyidodecyi oleate | PEG-9 stearyl stearate |
| Maleated soybean oil | 2-Octyidodecyl ricinoleate | PEG-10 stearyl stearate |
| Mango extract | Octyidodecyl stearate | PEG-12 |
| 3-Methyl-1,3-butanediol | Octyidodecyl stearoyl stearate | PEG-12 dioleate |
| Methyl acetyl ricinoleate | Octyl hydroxystearate | PEG-12 palm kernel glycerides |
| Methyl gluceth-20 | Octyl isononanoate | PEG-15 cocamine phosphate oleate |
| Methyl gluceth-20 benzoate | Octyl neopentanoate | PEG-18 |
| Methyl gluceth-20 distearate | Octyl octanoate | PEG-20 |
| Methyl hydroxystearate | Octyl oleate | PEG-20 hydrogenated castor oil isostearate |
| Methyl ricinoleate | Octyl palmitate | PEG-20 hydrogenated castor oil triisostearate |
| Microcrystalline wax | Octyl pelargonate | PEG-20 hydrogenated lanolin |
| Mineral oil | Octyl stearate | PEG-24 hydrogenated lanolin |
| Mink oil | Ointment base | PEG-24 PABA |
| Mixed mucopolysaccharides | Oleamine oxide | PEG-25 propylene glycol stearate |
| Musk rose oil | Oleic alcohol | PEG-40 hydrogenated castor oil isostearate |
| Myreth-3 | Oleic-palmitoleic-linoleic glycerides | PEG-40 hydrogenated castor oil laurate |
| Myreth-3 caprate | Oleostearine | PEG-40 hydrogenated castor oil triisostearate |
| Myreth-3 laurate | Oleyl alcohol | PEG-40 jojoba oil |
| Myreth-3 myristate | Oleyl erucate | PEG-50 hydrogenated castor oil laurate |
| Myreth-3-octanoate | Oleyl oleate | PEG-50 hydrogenated castor oil triisostearate |
| Myristyl alcohol | Olive oil | PEG-70 mango seed glycerides |
| Myristyl lactate | Orange roughy oil | PEG-75 |
| Myristyl myristate | Orange wax | PEG-75 illipe butter glycerides |
| Myristyl octanoate | Palmitic acid | PEG-75 lanolin |
| Myristyl propionate | Palm kernel glycerides | PEG-75 shea butter glycerides |
| Myristyl stearate | Palm oil | PEG-150 |
| Neatsfoot oil | d-Panthenyl triacetate | PEG-PPG-17-6 copolymer |
| Neem oil | Partially hydrogenated canola oil | Pentaerythritol dioleate |
| Neopentyl glycol dicaprate | Partially hydrogenated soybean oil | Pentaerythritol stearate |
| Pentaerythritol tetralaurate | PPG-3 myristyl ether | Propylene glycol dipelargonate |
| Pentaerythritol tetraoctanoate | PPG-5-buteth-7 | Propylene glycol isoceteth-3 acetate |
| Pentaerythritol tetrapelagonate | PPG-5 butyl ether | Propylene glycol isostearate |
| Pentaerythriyl tetracaprylate-caprate | PPG-5 lanolin wax | Propylene glycol laurate |
| Pentaerythriyl-tetracaprylate-tetracaprate | PPG-5-laureth-5 | Propylene glycol myristate |
| Pentaerythriyl tetraisononanoate | PPG-5 pentaerytyl ether | Propylene glycol myristyl ether acetate |
| Pentaerythriyl tetraisostearate | PPG-7-buteth-10 | Propylene glycol stearate, SE |
| Pentaerythriyl tetraoleate | PPG-8-SMDI copolymer | Rapeseed oil |
| Pentaerythriyl tetrastearate | PPG-9 | Rice bran oil |
| Petrolatum | PPG-9-buteth-12 | Rose hips oil |
| Phenyl dimethicone | PPG-9 butyl ether | Safflower oil |
| Phenylmethylpolylsiloxanes | PPG-10 butanediol | Salmon egg extract |
| Phenyl trimethicone | PPG-10 cetyl ether | Sesame oil |
| Pistachio nut oil | PPG-10 methyl glucose ether | Shark liver oil |

TABLE 2-continued

| | | |
|---|---|---|
| Placental enzymes | PPG-10 oleyl ether | Shea butter |
| Poloamer 105 benzoate | PPG-11 stearyl ether | Shea butter, ethoxylated |
| Poloxamer 182 dibenzoate | PPG-12-buteth-16 | Sitostearyl acetate |
| Polybutene | PPG 12-PEG-50 lanolin | Skin lipids |
| Polydecene | PPG-12 PEG-65 lanolin oil | Sodium C8-16 isoalkylsuccinyl lactoglobulin sulfonate |
| Polyethylene glycol | PPG-12/SMDI copolymer | Sodium glyceryl oleate phosphate |
| Polyglycerol-10 tetra oleate | PPG-14 butyl ether | Sodium hyaluronate |
| Polyglyceryl-2 diisostearate | PPG-15 butyl ether | Sodium polymethacrylate |
| Polyglyceryl-2 tetraisostearate | PPG-15 stearyl ether | Sorbeth-20 |
| Polyglyceryl-2 triisostearate | PPG-15 stearyl ether benzoate | Sorbitan isostearate |
| Polyglyceryl-3 diisostearate | PPG-16 butyl ether | Sorbitan palmitate |
| Polyglyceryl-3 distearate | PPG-18 butyl ether | Sorbitan sesquioleate |
| Polyglyceryl-3 stearate | PPG-20 | Sorbitan sesquistearate |
| Polyglyceryl-10 decaoleate | PPG-20-buteth-30 | Sorbitan trioleate |
| Polyglyceryl-10 decastearate | PPG-24-glycereth-24 polyglycol copolymer | Soybean oil |
| Polyisobutene (hyd.) | PPG-26 | Spermaceti |
| Polyisobutene/isohexopentacentahectane | PPG-27 glyceryl ether | Sphingolipids |
| Polyisobutene/isooctahexacontane | PPG-28-buteth-35 | Squalene |
| Polyisobutene/isopentacontaoctane | PPG-30 | Squalene |
| Polyisoprene | PPG-30 cetyl ether | Stearamidoproyl dimethyl cetearyl diammonium tosylate |
| Polyoxyethylene-15 cocoamine phosphate-oleate complex | PPG-40 butyl ether | Stearamine oxide |
| Polyoxyethylene polyoxypropylene glycol | PPG-50 cetyl ether | Steareth-4 stearate |
| Polyquaternium-2 | PPG-50 oleyl ether | Stearic acid |
| Polysiloxane polyalkylene copolymer | PPG-51-SMDI copolymer | Stearic hydrazide |
| Polysorbate 40 | PPG-53 butyl ether | Stearoxy dimethicone |
| Potassium dimethicone copolyol phosphate | Propylene glycol ceteth-3 acetate | Stearoxymethicone-dimethicone copolymer |
| PPG-2-buteth-3 | Propylene glycol dicaprylate | Stearyl behenate |
| PPG-2 lanolin ether | Propylene glycol dicaprylate-dicaprate | Stearyl benzoate |
| PPG-2 myristyl ether propionate | Propylene glycol diisostearate | Stearyl erucate |
| PPG-3 hydrogenated castor oil | Propylene glycol dioctanoate | Stearyl heptanoate |
| Stearyl propionate | | |
| Stearyl stearate | | |
| Stearyl stearoyl stearate | | |
| Sunflower seed oil | | |
| Sweet almond oil | | |
| Synthetic wax | | |
| Tallow | | |
| Tetradecycleicosyl stearate | | |
| Tocopheryl acetate | | |
| Tribehenin | | |
| Tricaprin | | |
| Tricaprylin | | |
| Tridecyl behenate | | |
| Tridecyl cocoate | | |
| Tridecyl erucate | | |
| Tridecyl neopentanoate | | |
| Tridecyl octanoate | | |
| Tridecyl stearate | | |
| Tridecyl stearoyl stearate | | |
| Tridecyl trimellitate | | |
| Triheptanoate | | |
| Triisocetyl citrate | | |
| Triisostearin | | |
| Triisostearyl citrate | | |
| Triisostearyl trilinoleate | | |
| Trilaurin | | |
| Trilinoleic | | |
| Trimethylopropane-tricaprylate-tricaprate | | |
| Trimethylolpropane tricocoate | | |
| Trimethylolpropane trilaurate | | |
| Trimyristin | | |
| Trioctanoate | | |
| Trioctanoin | | |
| Trioctyl citrate | | |
| Trioctyldodecyl citrate | | |
| Triolein | | |
| Tripalmitin | | |
| Tripropylene glycol citrate | | |
| Tristearin | | |
| Triundecanoin | | |
| Vegetable glyceride, fractioned | | |
| Walnut oil | | |

TABLE 2-continued

Wheat germ oil
Yeast extract (*Saccharomyces cerevisiae*)

The oil phase or carrier of the present invention is present at an "effective level" which is a level which provides the desired skin benefits of the particular ingredients. Typically, the oil phase is present at a level of from about 0.1% to about 36%, preferably from about 0.2% to about 6%, by weight of the composition.

Surfactant

A surfactant must be used in the present invention. Surfactants are known in the art of forming oil-in-water emulsions. Preferably, a combination of surfactants are used for improved stability.

Surfactants suitable for use herein are surfactants which do not have a high level of interaction with the cyclodextrin, thus optimizing the odor absorbing capability of cyclodextrin. Extensive interaction is not desirable as it may diminish the ability of the cyclodextrin to complex with odor causing compounds and the ability of the surfactant to blend the oil and water phases.

The surfactants optimize both the odor absorbing characteristic of cyclodextrin and the blending ability of the surfactant. Such surfactants, when added to an aqueous cyclodextrin solution, provide a surfactant/cyclodextrin solution which demonstrate odor absorption similar to the same cyclodextrin solution without the surfactant. Not desirable are surfactants which, when added to an aqueous cyclodextrin solution, provide a surfactant/cyclodextrin solution which demonstrate odor absorption similar to pure water.

The surfactants can be identified using the procedure which follows. First, within an equilibrium chamber, a paper membrane is sealed to a test cell and wetted with a test sample mixture; or, for purposes of establishing a water control and a cyclodextrin control, the membrane is wetted with water or aqueous cyclodextrin. Test sample mixtures comprise mixtures of a solution of aqueous cyclodextrin and a surfactant or a combination of surfactants. Second, an odor causing challenge compound is injected into the equilibrium chamber and allowed to equilibrate through the paper membrane. The odor causing challenge compounds selected should be those which uncomplexed cyclodextrin is capable of absorbing such as isovaleric acid. Third, after a finite time air in the equilibrium chamber enveloping the test cell is pulled through a Drager tube, which results in a color change within the chamber. (Drager tubes are commercially available from Lab Safety, Danesville, Wis.). The distance of color movement up the Drager tube corresponds to the remaining (or uncomplexed) concentration of odorous material within the Drager tube. Replicates of this entire procedure are performed and averages are taken. Any similar procedure such as Gas Chromatograph Head Space Analysis may also be used.

The results from each test sample mixture are then compared to the results of the water control and the cyclodextrin control. As used herein, the phrase "odor capture" refers to the amount of cyclodextrin which complexes with the challenge compound. Thus, a high level of odor capture results in a low level of remaining challenge compound. The surfactant should provide a surfactant/cyclodextrin solution which demonstrates more odor capture than the water control. Preferred surfactants provide a surfactant/cyclodextrin solution which demonstrates no less than about 25%, more preferred no less than about 50%, and even more preferred no less than about 75%, of the level of odor capture as the cyclodextrin control.

Most preferred surfactants provide about the same level of odor capture as the cyclodextrin control.

Additionally, it is preferable for formation of oil-in-water emulsions that the selected surfactant have a hydrophilic/lipophilic balance ("HLB") of about 8–18. The term HLB is known in the art, for example in U.S. Pat. No. 2,677,700 to Jackson et al., issued May 4, 1954, and incorporated herein by reference. Because of the uniqueness of many of the surfactants mentioned below, they will demonstrate lipophilic behavior different from hydrocarbon lipophiles. Consequently, the HLB values may not correlate exactly with the HLB values for ethylene oxide/hydrocarbon surfactants. Overall, the preferred surfactants for use herein include block copolymers of ethylene oxide and/or propylene oxide and polyalkyleneoxide polysiloxanes. Most preferred are mixtures of at least one of each of block copolymers of ethylene oxide and/or propylene oxide and polyalkyleneoxide polysiloxanes.

Block polyoxyethylene-polyoxypropylene polymeric compounds which are compatible with most cyclodextrins include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Block polymer surfactant compounds designated Pluronic® and Tetronic® are commercially available from the BASF-Wyandotte Corp.

Typical block copolymers of ethylene oxide and/or propylene surfactants include:

Pluronic® surfactants: $H(EO)_n(PO)_m(EO)_nH$;
Reverse Pluronic® surfactants: $H(PO)_n(EO)_m(PO)_nH$;
Tetronic® surfactants:

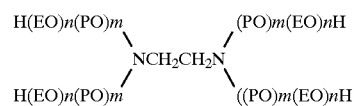

and/or
Reverse Tetronic® surfactants:

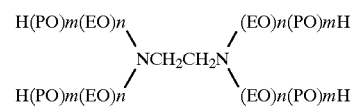

wherein EO is an ethylene oxide group, PO is a propylene oxide group, and n and m are numbers that indicate the average number of the groups in the surfactants. The average molecular weight of the polyoxypropylene polymers in the mixture is between about 900 to about 25,000 and the oxyethylene groups constitute between about 10 to about 90 weight percent of the oxyethylene/oxypropylene mixture.

Non-limiting examples of surfactants useful herein having an HLB of about 8 to 18 include: Pluronic® surfactants L10, L43, L44, L63, L64, L65, P75, P84, P85, P103, P104, P105, P123, and mixtures thereof; Reverse Pluronic® surfactants 10R5, 17R4,17R8, 22R4,25R4, 25R5, 25R8, and mixtures thereof; Tetronic® surfactants: 304, 504, 704, 707, 904, 1104, 1304, 1504, and mixtures thereof; and Reverse Tetronic® surfactants 50R4, 50R8, 70R4, 90R8, 110R7150R8, and mixtures thereof; and mixtures thereof.

More detailed examples of the aforementioned surfactants and methods of making them are described in U.S. Pat. No. 2,674,619, Lundsted et al., issued Apr. 6, 1954; U.S. Pat. No. 3,036,118, Jackson et al., issued May 22, 1962; and U.S. Pat. No. 2,979,528, Lundsted et al., issued Apr. 11, 1961; all incorporated herein by reference in their entireties.

Polyalkyleneoxide polysiloxanes are defined by the general formula:

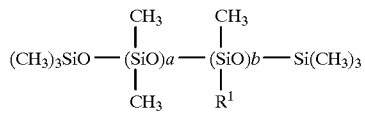

wherein a+b are from about 1 to about 50, preferably from about 3 to about 30, more preferably from about 10 to about 25, and $R^1$ is mainly one or more random or block poly (ethyleneoxide/propyleneoxide) copolymer groups having the general formula:

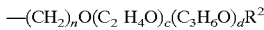

wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group. Examples of such compounds suitable herein include: Silwet® L-7600, L-7602, L-7604, L7605, L-7657, and mixtures thereof; all commercially available from OSi Specialties, Endicott, N.Y.

The molecular weight of the oxyalkylene group (R1) is less than or equal to 10000. Preferably, the molecular weight of the oxyalkylene group is less than or equal to about 8000, and most preferably ranges from about 300 to 5000. Thus, the values of c and d can be those numbers which provide molecular weights within these ranges. However, the number of oxyethylene units (—$C_2H_4O$) in the polyoxyalkylene groups (R1) must be sufficient to render the polyalkyleneoxide polysiloxane water dispersible or water soluble. It is understood that when c is a positive number, the oxyethylene and oxypropylene units (—$C_3H_6O$) can be distributed randomly throughout the polysiloxane chain or in respective blocks of oxyethylene and oxypropylene units or a combination of random and block distributions. The preparation of polyalkyleneoxide polysiloxanes is well known in the art. Such compounds can be prepared according to the procedure set forth in U.S. Pat. No. 3,299,112, incorporated herein by reference.

The total surfactant level used in the present compositions is from about 0.05% to about 15%, more preferably from about 0.1% to about 12%, by weight of the composition. If a hydrophobic antimicrobial agent is included, more surfactant(s) should be included, typically from about 0.5% to about 10%, by weight of the composition.

Aqueous Carrier

The cyclodextrins useful in the methods of the present invention should be solubilized in and dispersed in an aqueous carrier. The dilute aqueous solution provides the maximum separation of cyclodextrin molecules on the skin and maximizes the chance that an odor molecule will interact with a cyclodextrin molecule. An aqueous carrier is also beneficial in that it provides a clean, convenient means for applying the cyclodextrin to the desired skin sites. Additionally, an aqueous carrier may impart a degree of cleaning power in and of itself via washing away skin cell debris and skin secretions which bacteria feed upon, as well as the bacteria themselves.

The term "aqueous carrier", as used herein, means water and/or any water soluble materials suitable for use as solvents. Any water may be used, such as distilled, deionized, or tap water. Water not only serves as the liquid carrier for the cyclodextrins, but it also facilitates the complexation reaction between the cyclodextrin molecules and any malodorous molecules that are on the skin site when the composition is applied.

The aqueous carrier of the present invention will typically comprise from about 80% to about 98% of the present invention's composition. Preferably the compositions comprise the aqueous carrier at from about 85% to about 95%, by weight of the composition.

Antimicrobial Preservative

The compositions may optionally but preferably contain solubilized, mild, water-soluble, antimicrobial preservatives which are effective for inhibiting and/or regulating microbial growth in the composition. Contamination of the present compositions by microorganisms and subsequent microbial growth can result in unsightly or malodorous compositions. Similarly, microorganisms are typically found in cyclodextrin supplies and their growth in aqueous solutions is possible. The inclusion of the antimicrobial preservatives aids in increasing storage stability of the present invention. When included for preservative action, the water-soluble antimicrobials are present in an effective amount. The phrase "effective amount" of water-soluble antimicrobial preservative as used herein means a level sufficient to prevent spoilage, or prevent growth of microorganisms inadvertently added to the composition, for a specific period of time. If antimicrobial action on the skin is desired, the water-soluble antimicrobials must be present at a level effective to perform the preservative action discussed above and to kill and/or prevent growth of microorganisms on the skin.

Antimicrobials useful herein include biocidal and biostatic compounds (substances that kill microorganisms and/or regulate the growth of microorganisms). Suitable water-soluble antimicrobial preservatives have a solubility of 0.3% or greater. In addition, suitable preservatives are those which can come into contact with skin without high irritation potential. Preservatives suitable for use in the present compositions are fully described in *The Theory and Practice of Industrial Pharmacy,* by Lachman, Lieberman, Kanig, 3rd. Edition, pages 466–467 and 520–522 (1986), and U.S. Pat. No. 5,534,165, to Pilosof et al., issued Jul. 9, 1996, both of which are incorporated herein by reference.

It is preferable to use a broad spectrum preservative such as one that is effective both on bacteria (both gram positive and gram negative) and fungi. A limited spectrum preservative such as one that is only effective on a single group of microorganisms, for example fungi, can be used in combination with a broad spectrum preservative or other limited spectrum preservatives with complimentary and/or supplementary activity. A mixture of broad spectrum preservatives can also be used.

Preferred water-soluble preservatives include the following: sodium hydroxymethylglycinate (i.e. Suttocide® A., from Sutton Labs Chatham, N.J.), cyclic organic nitrogen compounds including imidazolidinedione compounds (such as dimethyloldimethylhydantoin i.e., Glydant® Plus from Lonza, Fair Lawn, N.J., diazolidinyl urea and imidazolidinyl urea) and polymethoxy bicyclic oxazolidine; phenyl and phenoxy compounds including benzyl alcohol, 2-phenoxyethanol and hexamidine isethionate; quaternary ammonium compounds including polyhexamethylene biguanide; low molecular weight aldehydes including formaldehyde and glutaraldehyde; halogenated compounds including chlorhexidine, chlorobutanol, and dibromopropamidine; and mixtures thereof.

Preferred levels of preservative are from about 0.0001% to about 0.6%, more preferably from about 0.0002% to about 0.55%, most preferably from about 0.0003% to about 0.5%, by weight of the composition.

Hydrophobic Antibacterial Agents

Optionally, the compositions of the present methods may include hydrophobic antibacterial compounds to help destroy and/or control the amount of bacteria present on the skin, which aids in body odor control. However, hydrophobic antibacterial agents can form inclusion complexes with the cyclodextrin molecules and compete with the malodorous molecules for the cyclodextrin cavities, thus rendering the cyclodextrins ineffective as odor controlling actives. To account for this, the level of cyclodextrin may be increased as desired. Hydrophobic antibacterials useful in the present invention include triclosan, triclocarbon, eucalyptol, menthol, methylsalicylate, thymol, and mixtures thereof. Preferred are triclosan and triclocarbon. When included in the present compositions, the hydrophobic antibacterials may be at a level of from about 0.1% to about 1.5% and preferably from about 0.1% to about 0.3%, by weight of the composition.

pH

Aqueous compositions of the present invention should have a pH of from about 3 to about 10, preferably from about 3.5 to about 8, more preferably from about 3.5 to about 6. Some conventional buffering agents are known in the prior art which may be used to adjust the pH to the desired level if necessary. For example, combinations of salts and acids, such as the following examples: sodium lactate, sodium citrate, potassium phosphate, lactic acid, citric acid, phosphoric acid, hydrochloric acid and sodium hydroxide are useful. Some of the effectiveness of these ingredients may be lost as they complex with the cyclodextrin, so care is taken in formulating to adjust for that. Other optional buffers appear in *The Theory and Practice of Industrial Pharmacy,* Lachman, Lieberman and Kanig, Third Edition, incorporated herein by reference.

Other Components

The compositions may also optionally comprise low molecular weight polyols. The phrase "low molecular weight polyols", as used herein, refers to linear organic compounds with more than one alcohol functional group per molecule wherein the molecular weight is less than 95. Low molecular weight polyols with relatively high boiling points, as compared to water, such as propylene glycol and glycerol are preferred ingredients for improving environmental odor control performance of the present compositions. Cyclodextrins prepared by processes that result in a level of such polyols are highly desirable, since they can be used without removal of the polyols.

Optimally, the low molecular weight polyols will be added at a level effective to assist in complex formation without significantly reducing available cyclodextrin capacity to absorb the malodor molecules having larger sizes. Typically, low molecular weight polyols are added to the composition of the present invention at a level of from about 0.01% to about 1%, by weight of the composition, preferably from about 0.02% to about 0.5%, more preferably from about 0.03% to about 0.3%, by weight of the composition.

The compositions can also optionally contain adjunct odor-controlling materials, such as zinc salts, water-soluble cationic polymers, water-soluble anionic polymers, water-soluble carbonate salts, water-soluble bicarbonate salts, zeolites, and activated carbon; chelating agents; colorants; and/or antiperspirants.

Optionally, but highly preferred, the present invention can include zinc salts for added odor absorption and/or antimicrobial benefit for the cyclodextrin solution. Zinc compounds have been used most often for their ability to ameliorate malodor, e.g., in mouth wash products, as disclosed in U.S. Pat. Nos. 4,325,939, issued Apr. 20, 1982 and 4,469,674, issued Sept. 4, 1983, to N. B. Shah, et al., both of which are incorporated herein by reference in their entireties. Highly-ionized and water soluble zinc salts, such as zinc chloride, provide the best source of zinc ions. The zinc salts, zinc chloride and zinc phenolsulfonate, are preferred for use in the skin composition of the present invention; although others may also fall within the scope of the present invention. However, care must be taken in selecting zinc salts, as well as their levels, since some may be irritants to the skin and therefore are not preferred for use in the present invention.

These zinc salts aid in absorbing low molecular weight amine and sulfur-containing compounds. Low molecular weight amines and/or low molecular weight sulfur-containing materials such as sulfide and mercaptans; are components of many types of malodors such as food odors (garlic, onion), breath odor, urine odors, and particularly body/perspiration odor. When zinc salts are added to the composition of the present invention they are typically present at a level of from about 0.1% to about 10%, preferably from about 0.2% to about 8%, more preferably from about 0.3% to about 5%, by weight of the composition.

Some water-soluble polymers such as water-soluble cationic polymer and water-soluble anionic polymers can be used in the composition of the present invention to provide additional odor control benefits. Water-soluble cationic polymers such as those containing amino functionalities, amido functionalities, and mixtures thereof, are useful in the present invention to control certain acid-type odors. Water-soluble anionic polymers such as polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued March 20, 1990, to N. Kobayashi and A. Kawazoe, incorporated herein by reference, in its entirety. Another example of water-soluble polymers containing both cationic and anionic functionalities is a copolymer of dimethyldiallyl ammonium chloride and acrylic acid, commercially available under the trade name Merquat 280® from Calgon. While the aforementioned water soluble polymers are useful in the present invention, when using these materials, care must be taken to insure no residual acrylic acid is present due to safety concerns associated with the presence of acrylic acid.

Water-soluble alkali metal carbonate and/or bicarbonate salts, such as sodium bicarbonate, potassium bicarbonate, potassium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention, it is preferred that incompatible metal salts not be present in the invention. Preferably, when these salts are used, the composition should be essentially free of zinc and other incompatible metal ions, e.g., Ca, Fe, etc. which form water-insoluble salts.

Aminocarboxylic acid chelating agents such as ethylenediaminetetraacetic acid (EDTA) can optionally be added to the composition of the present invention in order to enhance the activity of the water-soluble, antimicrobial preservative. When a chelating agent is added to the composition of the present invention, it is typically present at a level of from about 0.001% to about 0.3%, preferably from about 0.001% to about 0.2% by weight of the composition.

Zeolites can also be used in the present invention. A preferred class of zeolites are characterized as "intermediate" silicate/aluminate zeolites, particularly for use in absorbing amine-type odors. "High" zeolites are preferred for control of sulfur-containing odors, e.g., thiols, mercaptans. Zeolites are explained more fully in U.S. Pat. No. 5,429,628, to Trinh et al., issued Jul. 4, 1995, which is incorporated herein by reference in its entirety.

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

Colorants and dyes can be optionally added to the odor absorbing compositions for visual appeal and performance impression. When colorants are used, care must be taken in the selection of choosing dye levels that will not color skin. Preferred colorants for use in the present compositions are highly water-soluble dyes, e.g., acid blue 3, acid blue 104, acid green 1, acid green 25, acid yellow 3, acid yellow 73 sodium salt, D&C green no. 5, 6 & 8, D&C yellow no. 7, 8, 10 & 11, D&C violet no. 2, FD&C blue No. 1 & 2, FD&C green no. 3, FD&C yellow no. 5 & 6, and mixtures thereof.

Optionally, the present skin composition may also comprise known antiperspirants and/or other known deodorant compositions not explicitly disclosed previously. Examples of antiperspirants appropriate for aqueous solutions include aluminum-zirconium tetrachlorohydrex glycine, aluminum-zirconium pentachlorohydrate, aluminum sesquichlorohydrate, or aluminum chlorhydrate and mixtures thereof.

PROCESS OF MAKING COMPOSITIONS

The compositions used in the present method may be prepared by oil-in-water emulsion techniques such as are commonly known in the art. Examples of such techniques are described in Remington's Pharmaceutical Science, Eighteenth Edition, pp. 304–306, 1990, incorporated herein by reference. The compositions of the present method also may be prepared by a process comprising the steps of: making a mixture by mixing a surfactant(s) and an oil phase until homogenous and adding an aqueous phase with mixing until the mixture is homogenous. Making a solution by adding cyclodextrin with an aqueous phase with mixing until the cyclodextrin dissolves. Making a second mixture by mixing the solution with the mixture until the second mixture is homogenous. Where desired, the second mixture may be further diluted by adding an aqueous phase with mixing until homogenous. Where hydrophobic antimicrobials also comprise the compositions, the process of making the mixture in the first step additionally comprises adding a premix with mixing to the surfactant(s) and the oil phase until homogenous, wherein the premix is prepared by mixing a hydrophobic antimicrobial with a surfactant(s) until the premix is homogenous. The term "homogenous", as used herein, means a uniformly dispersed solution. Homogeneity is indicated by a composition which is substantially smooth, lump-free and uniform in appearance. A stable emulsion remains homogeneous over a given period which is determined by the required shelf life of the composition.

As an alternative to making the mixture by mixing a surfactant(s), an oil phase, and an aqueous phase; an emulsion concentrate comprising a surfactant(s), an oil phase, and a minimal amount of aqueous carrier may be used. Emulsion concentrates useful in the present invention will be from about a 3-fold to about a 20-fold concentrate. The concentrated emulsion may then be diluted by adding aqueous carrier followed by addition of the remaining ingredients as discussed above.

Other variations to the above processes of making should be readily apparent to those of ordinary skill in the art. For instance, the mixture could be made in one step by addition and mixing of each of the ingredients. Alternatively, less than all of the ingredients may be pre-combined for subsequent combination with other ingredients or with other pre-combined ingredients to form the composition.

Equipment suitable for forming the mixtures and emulsion may be selected from those which are known or become known in the art. For example, suitable apparatii include dual propeller blade mixers, and sonifiers. A turbine mixer and an in-line homogenizer using tandem rotor-stators, described in the above-referenced U.S. Pat. No. 5,043,155, may also be used.

The resultant emulsion containing the ingredients in their total amounts has a preferred viscosity at room temperature (i.e., 20°–25° C.) in the range of from about 10 to about 200 centipoise more preferably from about 15 to about 150 centipoise; most preferably from about 20 to about 100 centipoise.

Since the compositions of the present method are to be applied directly to the skin and/or hair, various applicators are useful for delivering the compositions to the entire body for maximum odor control. For example, the compositions are preferably deposited on a paper product such as a wipe which later is contacted with the skin to transfer the composition to the skin.

Any wipe structures and/or methods of making the wipe structures commonly known in the art may be used in the compositions of the present method. The wipe comprises a flexible dispensing means. The term "flexible dispensing means", as used herein, includes papers, cloths, non-wovens, films, foams, foam sheets, sponges, rollers, pads, tissues, cotton balls, and the like. Preferred wipe substrates comprise a porous material, such as the non-woven substrates, foams, or sponges, which are capable of holding the composition within the pores of the substrates. Examples of cellulosic non-wovens particularly useful and economic in the present invention are described in U.S. Pat. No. 4,191,609, Trokhan, issued Mar. 4, 1980. Further description of useful wipes and methods of making said wipes are found in World Patent 95/17175, to Mitra et. al, publication date of Jun. 29, 1995. Both references are incorporated herein by reference in their entireties.

Techniques for combining the wipe substrates with the composition of the present method are well known in the art. Examples of common methods of combining the composition to the wipe substrate may involve coating, immersing, dipping, or spraying, the wipe substrate with the composition of the present invention. The composition is added to the wipe substrate at level sufficient to provide the desired odor control and/or other desired skin benefits of the present invention. A convenient method of combining the composition of the present invention with the chosen substrate is to place the substrate inside an open package which will ultimately house the finished product until use. The composition is poured onto the substrate and allowed to distribute throughout. It is preferred that the homogenous composition is poured onto each wipe individually rather than onto a stack of wipes. The package is then closed and the wipes ready for use. Packages suitable for use herein are any packages commonly known in the art and include resealable packages and those suitable for one time use.

The composition of the present invention method can also be delivered as a liquid via a spray dispenser or a bottle. Preferred is a manually activated spray dispenser to avoid the use of aerosols which may be irritating to sensitive areas of the body. Spray dispensers useful in the present invention are described more fully in U.S. Pat. No. 5,534,165 which is incorporated herein by reference in its entirety.

The following non-limiting examples illustrate the formulations and methods of use of the present invention.

EXAMPLES I, II, and III

| Ingredients | Example I Wt. % | Example II Wt. % | Example III Wt. % |
|---|---|---|---|
| Pluronic ® L-44 |  | 0.15 | 0.30 |
| Pluronic ® L-43 | 0.20 |  |  |
| Silwet ® L-7657 |  |  | 0.30 |
| Silwet ® L-7605 |  | 0.15 |  |
| Silwet ® L-7600 | 0.20 |  |  |
| Dimethicone | 3.0 | 2.0 | 2.0 |
| Propylene glycol | 0.16 | 0.12 |  |
| Citric acid | 0.03 | 0.03 | 0.03 |
| Disodium phosphate | 0.02 | 0.02 | 0.02 |
| Glydant ® Plus | 0.30 | 0.20 |  |
| Suttocide ® A |  | 0.25 | 0.50 |
| Tetrasodium EDTA | 0.10 | 0.10 |  |
| Hydroxy propyl beta cyclodextrin | 1.00 | 1.50 | 0.5 |
| Zinc phenolsulfonate | 1.01 |  | 1.01 |
| Triclosan |  |  | 0.15 |
| Distilled Water | Balance | Balance | Balance |

Alternatively, the hydroxy propyl beta cyclodextrin in the above examples could be substituted with other beta-cyclodextrins, alpha-cyclodextrins, gamma-cyclodextrins, or mixtures of these cyclodextrins and/or their derivatives.

Prepare Examples I–III as follows: Prepare a premix by mixing triclosan with about ⅙, by weight, of total Pluronic® L and/or Silwet® L (Example III only). Prepare a first mixture by mixing about 1% of water, by total formula weight, and the surfactant(s). For example III, preparing the first mixture also includes a final step of adding the premix with mixing. Using a sonifier, prepare a second mixture by adding dimethicone to the first mixture, then slowly adding about 1%–2% of water, by total formula weight. Prepare premix (a) by mixing hydroxypropyl beta cyclodextrin and about 1.5%–3% of water, by total formula weight; premix (b) by mixing zinc phenolsulfonate and about 2% of water, by total formula weight; premix (c) by mixing the ascorbic acid and about 2% of water by total formula weight; and premix (d) by mixing Glydant® Plus (and Suttocide® A) and propylene glycol (or water for Example III). Using a homogenizer, add remaining water to the second mixture to create a third mixture. Add premixes (a), (b), (c), and (d) to the third mixture using the homogenizer.

Preparation for Application to Skin

The solutions of the present invention, such as those formed from the examples may be loaded onto a wipe or poured into a spray device or poured directly onto the skin or cloth of the user's choosing for convenient application to the skin and/or hair.

To prepare wipes

Place dry fabric or wipe substance inside an open package which will ultimately contain the finished product. Where the composition comprises dimethicone, the mixture should once again be mixed vigorously to obtain a homogenous mixture. Pour the composition onto the fabric to distribute throughout. Close the package for storage until consumer use.

To prepare spray

Pour the composition into the selected spray package. Close the package for storage until consumer use.

EXAMPLE IV

A man is cooking fish and a spicy sauce requiring the dicing of garlic, onions, and various peppers. He is told that his hands and hair smell of these food odors and he wants to remove these odors from his body. The man rubs his hands and hair with wipes containing the composition in Example I. Each wipe deposits about 0.05 grams of environmental ordor-absorbing composition on the skin and hair. The man notices less odor after using the wipes.

EXAMPLE V

A woman finds that after she smokes a cigarette during a break at work, her hands and face smell of smoke and tobacco. She applies the composition from Example II via a hand-held trigger-spray bottle. She sprays the composition on her face and hands and the composition removes the residual smoke and tobacco odors which she found so disagreeable. (She deposits about 2 grams of environmental ordor-absorbing composition on the skin). This woman notices less odor and feels more comfortable returning to her desk after using the spray.

EXAMPLE VI

A man, on his way to an important meeting, stops to buy gasoline for his car. As he is filing the gas tank, gasoline splashes on his hands. The man wipes his hands on a paper towel but the gasoline odor remains on his hands. The man removes a small bottle from his gym bag which contains the composition of Example III. He opens the bottle and pours some of the composition on his hands, delivering roughly about 1 gram of the environmental odor-absorbing composition. He then smells his hands and notices that the gasoline odor is no longer present.

What is claimed:

1. A method of controlling environmental malodors on skin comprising the application to skin of a composition comprising:
   a. from about 0.1% to about 5%, by weight of the composition, of solubilized, water-soluble, uncomplexed cyclodextrin;
   b. an aqueous carrier;
   c. from about 0.1% to about 36%, by weight of the composition, of an oil phase selected from the group consisting of emollients, moisturizers, and skin protectants; and
   d. one or more surfactants each having a hydrophilic/lipophilic balance of about 8 to 18 and wherein each surfactant, when combined with an aqueous cyclodextrin solution, provides no less than 25% of odor capture as an aqueous cyclodextrin solution.

2. The method of claim 1 wherein the composition is deposited on a wipe which comprises a flexible dispensing means.

3. The method of claim 2 wherein the one or more surfactants is selected from the group consisting of block copolymers of polyoxyethylene-polyoxypropylene, polyalkyleneoxide polysiloxanes, and mixtures thereof.

4. The method of claim 3 wherein the composition further comprises one or more water-soluble antimicrobial preservatives.

5. The method of claim 4 wherein the composition further comprises one or more optional components selected from the group consisting of low molecular weight polyols; hydrophobic antimicrobials; zinc salts; water-soluble polymers; soluble carbonate and/or bicarbonate salts; chelating agents; zeolites; activated carbon; and mixtures thereof.

6. A method of controlling environmental malodors on skin comprising the application to skin of a composition comprising:
   a. from about 0.1% to about 5%, by weight of the composition, of solubilized, water-soluble, uncomplexed cyclodextrin;
   b. an aqueous carrier;
   c. from about 0.1% to about 36%, by weight of the composition, of an oil phase selected from the group consisting of emollients, moisturizers, and skin protectants;
   d. one or more surfactants each having a hydrophilic/lipophilic balance of about 8 to 18 and wherein each surfactant, when combined with an aqueous cylcodextrin solution, provides no less than about 50% a level of odor capture as an aqueous cyclodextrin solution; and
   e. a hydrophobic antimicrobial.

7. The method of claim 6 wherein the one or more surfactants each has a hydrophilic/lipophilic balance of about 8 to 18 and wherein each surfactant, when combined with an aqueous cylcodextrin solution, provides no less than about 75% a level of odor capture as an aqueous cyclodextrin solution.

8. The method of claim 7 wherein the one or more surfactants is selected from the group consisting of block copolymers of polyoxyethylene-polyoxypropylene, polyalkyleneoxide polysiloxanes, and mixtures thereof.

9. The method according to claim 8 wherein the hydrophobic antimicrobial is selected from the group consisting of triclosan, triclocarbon, eucalyptol, menthol, methylsalicylate, and thymol; and is present at a level of from about 0.1% to about 1.5% by weight of the composition.

10. The method of claim 9 wherein the composition further comprises one or more optional components selected from the group consisting of low molecular weight polyols; water-soluble antimicrobial preservatives; zinc salts; water-soluble polymers; soluble carbonate and/or bicarbonate salts; chelating agents; zeolites; activated carbon; and mixtures thereof.

11. The method of claim 10 wherein the composition is deposited on a wipe which comprises a flexible dispensing means.

12. The method of claim 10 wherein the composition is delivered as a liquid by a spray bottle.

13. A method of controlling environmental malodors on skin comprising the application to skin of a composition comprising:
   a. from about 0.1% to about 5%, by weight of the composition, of solubilized, water-soluble, uncomplexed cyclodextrin selected from the group consisting of hydroyxpropyl beta-cyclodextrin, methylated beta-cyclodextrins, and mixtures thereof;
   b. an aqueous carrier;
   c. from about 0.1% to about 36%, by weight of the composition, of an oil phase selected from the group consisting of emollients, moisturizers, and skin protectants;
   d. one or more surfactants each having a hydrophilic/lipophilic balance of about 8 to 18 and wherein each surfactant, when combined with an aqueous cylcodextrin solution, provides no less than about 50% of odor capture as an aqueous cyclodextrin solution;
   e. antimicrobials selected from the group consisting of a hydrophobic antimicrobial, a water-soluble hydrophilic antimicrobial preservative, and mixtures thereof; and
   wherein the composition is deposited on a wipe which comprises a flexible dispensing means.

14. The method according to claim 13 wherein the one or more surfactants are selected from the group consisting of block copolymers of polyoxyethylene-polyoxypropylene, polyalkyleneoxide polysiloxanes, and mixtures thereof.

15. The method according to claim 14 wherein the hydrophobic antimicrobial is selected from the group consisting of triclosan, triclocarbon, eucalyptol, menthol, methylsalicylate, and thymol; and is present at a level of from about 0.1% to about 1.5% by weight of the composition.

16. The method of claim 13 wherein the composition further comprises one or more optional components selected from the group consisting of low molecular weight polyols; zinc salts; water-soluble polymers; soluble carbonate and/or bicarbonate salts; chelating agents; zeolites; activated carbon; and mixtures thereof.

* * * * *